US009315497B2

(12) United States Patent
Verdecia Reyes et al.

(10) Patent No.: US 9,315,497 B2
(45) Date of Patent: Apr. 19, 2016

(54) TRICYCLIC AND TETRACYCLIC SYSTEMS WITH ACTIVITY ON THE CENTRAL NERVOUS AND VASCULAR SYSTEMS

(75) Inventors: Yamila Verdecia Reyes, Vedado (CU); Estael Ochoa Rodriguez, Vedado (CU); Alberto Ruiz Reyes, Vedado (CU); Yanier Nuñez Figueredo, Ciudad de la Habana (CU); Carmen Carillo Dominguez, Vedado (CU); Juan Enrique Tacoronte Morales, Cerro (CU); Livan Lázaro Alba Gutiérrez, Revolución (CU); Gilberto Lázaro Pardo Andreu, La Lisa (CU)

(73) Assignee: Centro de Investigacion Y Desarrollo de . . . (CIDEM) Laboratorio de Sintesis Organica de La Facultad . . ., Havana (CU)

( * ) Notice: Subject to any disclaimer, the term of this patent is extended or adjusted under 35 U.S.C. 154(b) by 286 days.

(21) Appl. No.: 13/500,983

(22) PCT Filed: Oct. 8, 2010

(86) PCT No.: PCT/CU2010/000004
§ 371 (c)(1),
(2), (4) Date: Apr. 9, 2012

(87) PCT Pub. No.: WO2011/041989
PCT Pub. Date: Apr. 14, 2011

(65) Prior Publication Data
US 2012/0202791 A1   Aug. 9, 2012

(30) Foreign Application Priority Data
Oct. 9, 2009   (CU) ............................... 2009 000172

(51) Int. Cl.
*A61K 31/551* (2006.01)
*A61K 31/5513* (2006.01)
*C07D 471/04* (2006.01)
*C07D 471/14* (2006.01)
*C07D 471/22* (2006.01)
*C07D 491/147* (2006.01)
*C07D 491/22* (2006.01)

(52) U.S. Cl.
CPC ............ *C07D 471/04* (2013.01); *C07D 471/14* (2013.01); *C07D 471/22* (2013.01); *C07D 491/147* (2013.01); *C07D 491/22* (2013.01)

(58) Field of Classification Search
CPC ........................... A61K 31/551; C07D 471/04
USPC ........... 514/219, 220; 540/493, 495, 555, 557
See application file for complete search history.

(56) References Cited

U.S. PATENT DOCUMENTS

| | | |
|---|---|---|
| 3,780,047 A | 12/1973 | Denzel et al. |
| 4,012,373 A | 3/1977 | Denzel et al. |
| 5,571,809 A | 11/1996 | Hargrave et al. |
| 5,610,158 A | 3/1997 | Bisaha et al. |
| 5,637,697 A | 6/1997 | Finch et al. |
| 5,658,901 A | 8/1997 | Claremon et al. |
| 2002/0103371 A1 | 8/2002 | Masciadri et al. |
| 2004/0157833 A1 | 8/2004 | Harris et al. |

FOREIGN PATENT DOCUMENTS

| | | |
|---|---|---|
| EP | 0 349 949 A2 | 1/1990 |
| EP | 0 491 218 A1 | 6/1992 |
| EP | 0 498 290 A1 | 8/1992 |
| EP | 0 558 104 A1 | 9/1993 |
| EP | 0 733 634 A1 | 9/1996 |
| EP | 1 157 992 A1 | 11/2001 |
| EP | 1 593 683 A2 | 11/2005 |

OTHER PUBLICATIONS

PCT/CU2010/00004; International Search Report; Jun. 24, 2011.

*Primary Examiner* — Brenda Coleman
(74) *Attorney, Agent, or Firm* — Marvin Feldman; Lackenback Siegel, LLP

(57) ABSTRACT

The present invention relates to chemistry and pharmacy and, in particular, to the production of novel molecular entities, tricyclic and tetracyclic derivatives of benzodiazepine, pyridodiazepine and pyrimidodiazepine type fused with 1,4-dihydropyridine derivatives, having an effect on the central-nervous and vascular systems. Derivatives containing a dihydropyridine ring are used, by means of reactions with compounds of the ortho-phenylenediamine, ortho-diaminopyridine and ortho-diaminopyrimidine type, and also subsequent conversions to some thereof, to obtain tricyclic and tetracyclic derivatives of general formula I-XII that contain a diazepine or diazepinone nucleus fused to a 1,4-dihydropyridine nucleus, in which the A ring is a substituted or unsubstituted benzene, pyridine or pyrimidine ring. These molecular entities exhibit GABAergica and modulating action in the case of calcium channels which can be used in the treatment of cardiovascular, cerebrovascular, neurodegenerative, neuropsychiatric and neurological disorders.

4 Claims, 2 Drawing Sheets

TRICYCLIC AND TETRACYCLIC SYSTEMS WITH ACTIVITY ON THE CENTRAL NERVOUS AND VASCULAR SYSTEMS

PRIOR RELATED APPLICATIONS

This application is a U.S. 371 National Phase Patent Application and claims priority to PCT Patent Application PCT/CU2010/000004, Filed Oct. 8, 2010, Published on Apr. 14, 2011 as Publication No. WO 2011/041989; PCT Patent Application PCT/CU2009/000172, Filed Oct. 9, 2009, which applications are incorporated herein in their entireties by reference thereto.

OBJECT OF THE INVENTION

This invention is related to chemistry and pharmacy and, in particular, to the production of novel molecular entities: tricyclic and tetracyclic derivatives of the benzodiazepine, pyridodiazepine, and pyrimidodiazepine type fused with 1,4-dihydropyridine derivatives, acting upon the Vascular and Central Nervous Systems. From derivatives containing a dihydropyridine ring reacting with compounds of the ortho-phenyldiamine, ortho-diaminopyridine, and ortho-diaminopyrimidine type, as well as some subsequent transformations thereof, tricyclic and tetracyclic derivatives of the I-XII general formula can be obtained, with a diazepine or diazepinone nucleus fused to a 1,4-dihydropyridine nucleus, wherein cycle A is a substituted or unsubstituted ring of benzene, pyridine or pyrimidine.

Such molecular entities have a GABAergic and modulating action on calcium channels that can be used to treat cardiovascular, cerebrovascular, neurodegenerative, neuropsychiatric, and neurologic diseases.

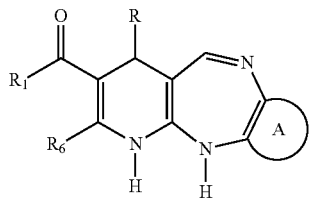

I

BACKGROUND OF THE INVENTION

This invention is related to the chemical and pharmaceutical branches, and more specifically with obtaining new molecular entities, synthetic variants of diazepine fused dihydropyridines of a general formula:

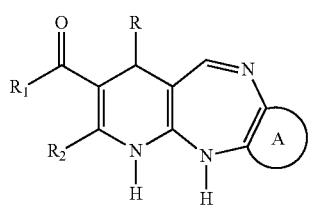

I

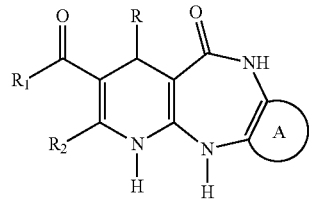

II

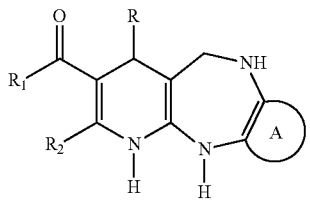

III

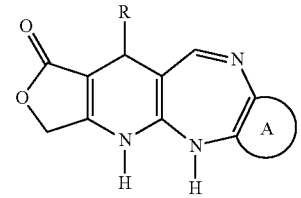

IV

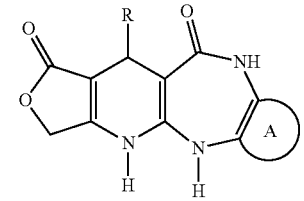

V

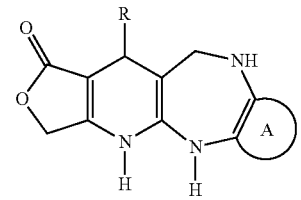

VI

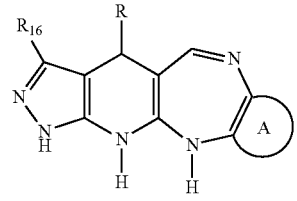

VII

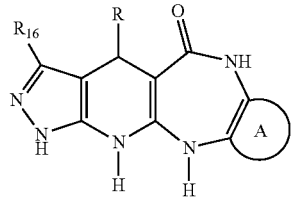

VIII

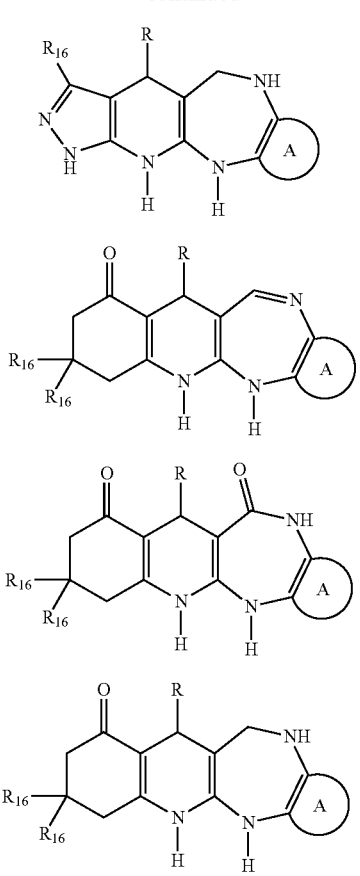

DESCRIPTION OF THE INVENTION

For compounds of general formula I, II, III, IV, V, VI, VII, VIII, IX, X, XI, and XII, R represents H, alkyl group (preferable straight or branched chain alkyl groups having up to 8 carbon atoms such as methyl, ethyl, propyl, butyl, pentyl, hexyl, heptyl, and octyl and all chain isomers thereof; as well as cyclic alkyl and alkyl-substituted compounds, preferably substituted with halogens; vinyl and vinyl-substituted compounds; and cycloalkyl chains, preferably the cyclohexyl group.

For compounds of general formula I, II, III, IV, V, VI, VII, VIII, IX, X, XI, and XII, R also represents an aryl group (benzyl, naphtyl, and substituted naphtyl or antracyl). The aryl and aryl-substituted group, represent, preferably, unsubstituted phenyl or phenyl substituted by one and up to five substituents independently selected from —$NO_2$, —$NH_2$, —OH, F, Cl, Br, I, —CN —$OCH_3$, —$N(CH_3)_2$), —$CH_3$, —$OCOCH_3$, —$COOCH_3$, —$OCF_3$, —SH, —NH(C=O)—$CH_3$, —CHO, —C=NH, —C=NH—$NH_2$, —C=NH—OH.

For compounds of general formula I, II, III, IV, V, VI, VII, VIII, IX, X, XI, and XII, R also represents heteroaryl, and heteroaryl substituted, wherein heteroaryl and heteroaryl substituted refer preferably to furfuryl, furfuryl substituted, pyrrolidyl, pyrrolidyl substituted, thiophenyl, thiophenyl substituted, pyridyl, (2-pyridyl, 3-pyridyl, and 4-pyridyl), pyridyl substituted, quinoline (2-quinoline, 3-quinoline, and 4-quinoline), pyrazolyl.

For compounds of general formula I, II, III, IV, V, VI, VII, VIII, IX, X, XI, and XII, R also represents an heteroaryl, preferably pyrrol, thiophen, and phenyl-substituted furan, wherein the phenyl group can be substituted in turn by one or more substituents selected from —CN, —C(C=O)—$CH_3$, F, Cl, Br, $NH_2$, $NO_2$.

For compounds of general formula I, II, and III, $R_1$ represents H, straight or branched chain alkyl group, and alicyclics, preferably having 1 to 16 carbon atoms.

For compounds of general formula I, II, and III, $R_1$ also represents OR', wherein R' can represent H or its Sodium (Na) and Potassium (K) salts; straight or branched chain alkyl groups having 1 to 24 carbon atoms, such as methyl, ethyl, propyl, isopropyl, butyl, isobutyl, sec-butyl, tert-butyl, pentyl, isopentyl, sec-pentyl, tent-pentyl, neopentyl, hexyl, isohexyl, sec-hexyl, tert-hexyl, heptyl, octyl, nonyl, decyl, undecyl, duodecyl, and all straight or branched chain position isomers thereof: —$(CH_2)$n-O—$(CH_2)$n-$CH_3$; —$(CH_2)$n-O—$(CH_2)$n-O—$(CH_2)$n-$CH_3$) wherein n is equal to 1 and less than 8, —$(CH_2)$n-CN, wherein n is a number between 1 and 8.

R' also represents lipid chains derived from mono or polyunsaturated fatty acids having up to 24 carbon atoms.

$R_1$ also represents —NHR", wherein R" independently represents H, straight or branched alkyl groups of carbonate chains having from 1 to 24 carbon atoms; —$(CH_2)$n-O—$(CH_2)$n-$CH_3$;   —$(CH_2)$n-O—$(CH_2)$n-O—$(CH_2)$n-$CH_3$) wherein n is a number between 1 and 8, —$(CH_2)$n-CN, wherein n=1-8; R" also represents lipid chains derived from mono and polyunsaturated fatty acids having up to 24 carbon atoms.

$R_1$ also represents —NHR''', wherein R''' independently represents —$(CH_2)$n-$NH_2$, wherein n is a number between 1 and 10, like for example (and preferably) —NH—$(CH_2)_6$—$NH_2$, —NH—$(CH_2)_3$—$NH_2$; $R_1$ also represents chains of the —NH—$(CH_2)$n-NH(C=O)—$R_3$ type, wherein n is a number between 1 and 10 and $R_3$ represents straight or branched alkyl groups; unsaturated alkylate remnants of the —$(CH_2)$n-C=C—$(CH_2)$n-$CH_3$ type, preferably long chains having up to 18 carbon atoms. For example (and preferably) —NH—$(CH_2)_6$—NH(C=O)—$C_{11}H_{23}$,   —NH—$(CH_2)_6$—NH(C=O)—$C_7H_{14}$—CH=CH—$C_8H_{17}$.

For compounds of general formula I, II and III, $R_1$ also represents amino acid remnants of the —NH—CH($R_4$)—COOH type, wherein $R_4$ is amino acid remnants, preferably from valine, phenylalanine, alanine, histidine, lysine, tryptophan, cysteine, leucine, tyrosine, isoleucine, proline, and methionine; R1 also represents small peptide chains having 2 and up to 12 amino acids, obtained by combining some of them, independently selected.

$R_1$ also represents —NH—OH; —NH—$NH_2$; —NH—NH—(C=O)—$NH_2$; —NH—NH—(C=S)—$NH_2$.

$R_1$ also represents —$NHR_5$, wherein $R_5$ is a thiazole or thiazole-substituted ring, 4-phenylthiazole or 4- phenylthiazole substituted; $R_5$ also represents a phenyl or a phenyl-substituted substituent.

For compounds of general formula I, II, and III, $R_2$ represents an alkyl or cycloalkyl group; alkyl groups can be straight or branched chained having 1 to 16 carbon atoms; —$(CH_2)$n-$NH_2$ groups, and —$(CH_2)$n-OH groups, wherein n is 1 to 8.

For compounds of general formula I, II, III, IV, V, VI, VII, VIII, IX, X, XI, and XII, cycle A is a 6-membered aromatic ring fused to the diazepine ring and represents a benzene or benzene-substituted ring, conforming a benzodiazepine, fused in such a way that it implies a structure and all its position isomers and all possible tautomers.

Benzene fused diazepine, represented as Ring A, is in turn substituted by one and up to four substituents independently selected from OH, COOH, $CH_3$, $NO_2$, $NH_2$, CHO (formyl group), halogens and combinations thereof.

The benzene group fused diazepine, represented by A, can also be replaced with carboxylic acid derivatives —C(C=O)—$R_6$, wherein $R_6$ represents O-alkyl, —O-aryl, $NH_2$, —NH-alkyl, —NH-aryl.

The benzene group fused diazepine, represented by A, can also be replaced by a —NH—C(C=O,S)—N($R_7$)$_2$ group, wherein $R_7$ is an H, or a small straight or branched chain alkyl group having 1 to 6 carbon atoms.

The benzene group fused diazepine, represented by A, can also be replaced by a —NH—(C=O,S)—$OR_7$ group, wherein $R_7$ is an H or small straight or branched chain alkyl group having 1 to 8 carbon atoms.

For compounds of general formula I, II, III, IV, V, VI, VII, VIII IX, X, XI, and XII, cycle A is also a 6-membered heterocyclic ring fused to the diazepine ring and represents a pyridine and pyridine-substituted ring, preferably with halogens. The pyridine ring can be fused to the diazepine ring in such a way that it will imply a structure and all possible position isomers and possible tautomers thereof.

For compounds of general formula I, II, III, IV, V, VI, VII, VIII IX, X, XI, and XII, cycle A is also a 6-membered heterocyclic ring fused to the diazepine ring and represents a pyrimidine substituted or unsubstituted ring, wherein one or both nitrogen atoms of the pyrimidine can be substituted by H, $CH_3$, OH, SH y $NH_2$ and combinations thereof, independently selected; the carbon atoms of the pyrimidine can be independently substituted by one or more substituents selected from H or $CH_3$ as well as OH, SH, $NH_2$, —C=O, —C=S, —C=NH, in such a manner that it implies a structure and all tautomeric forms, and position isomers and all tautomeric forms derived thereof.

For compounds of general formula I, II, III, IV, V, VI, VII, VIII, IX, X, XI, and XII, wherein cycle A is a pyrimidine-substituted ring, such pyrimidine ring can also be substituted in the carbon positions of the cycle by a $R_8$ substituent, wherein $R_8$ represents a straight or branched chain alkyl group having 1 to 6 carbon atoms, and preferably by an unsubstituted phenyl group or a phenyl group substituted by one and up to 5 substituents, independently selected from —$NO_2$, —$NH_2$, —OH, F, Cl, Br, I, —CN—$OCH_3$, —N($CH_3$)$_2$), —$CH_3$, —$OCOCH_3$, —$COOCH_3$, —$OCF_3$, —SH, —NH(C=O)—$CH_3$, —CHO, —C=NH, —C=NH—$NH_2$, —C=NH—OH, in such a manner that it implies a structure and all its possible position isomers and all tautomeric forms derived thereof.

These novel compounds can serve as a basis for therapeutic drugs to treat anxiety, ischemia, epilepsy, hypertension and other cardiovascular, cerebrovascular, neurodegenerative, neuropsychiatric, and neurological disorders, as well as other disorders related to the cardiovascular system.

Compounds of the I, II, III, X, XI, and XII type are obtained by fusing a 1,4-dihydropyridine derivative adequately substituted with a ortho-diamine disubstituted compound, ortho-phenylenediamine, ortho-diaminepyridines, ortho-diaminepyrimidines, to generate tricyclic (I, II, III) and tetracyclic (X, XI, and XII) compounds derived from diazepines or diazepinones fused with the 1,4-dihydropyridine derivative.

Transformation of compounds of general formula I, II, and III, can lead to the formation of tetracyclic structures of the IV, V, VI, VII, XIII, and IX type.

Due to the presence of a chiral carbon, new derivatives are obtained as a racemic modification, based on the racemic derivatives of 1,4-dihydropyridines, obtained in turn through their synthetic precursors, also obtained in a racemic form.

Enantiomers can be resolved and obtained separately, with an enantiomeric excess above 90% and is done by enantiomeric resolution of any of the baseline intermediaries or by enantiomeric resolution directly on the final product, preferably through enzymatic resolution, with previous chemical transformation (not always required) to facilitate the resolution process, and its subsequent transformation into the original resolved structure. All separated enantiomers were additionally characterized by measuring their specific rotation.

Benzodiazepines were the first pharmacological entities denominated privileged structures. Generally, most benzodiazepines act as depressant agents of the Central Nervous System by inhibiting the $GABA_A$ receptor, which is part of a bidirectional inhibiting system connected between several areas of the Central Nervous System. These derivatives have hypnotic, anxiolytic, anticonvulsant, amnesic, and muscle relaxant effects. They also have a vasodilator action and can be used in treating heart failure.

The 1,4-DHPs have been characterized as having a vasodilator and antihypertensive action. These structures have an antioxidant and neuro-protective activity.

In our molecular system, the presence of a fragment of 1,4-dihydropyridine that can interact as a calcium channel blocker, fused with a diazepine derivative, provides de possibility of using this new chemical entity as a potential therapeutic agent for treating cardiovascular, cerebrovascular, neurodegenerative, neuropsychiatric and neurological diseases.

After an analysis of the structure of the molecules tested and the exploratory behavior in rodents as an indicator of their interaction with the $GABA_A$ receptor, the use of synthetic variants of diazepines fused with DHPs for treating cerebrovascular, neurodegenerative, neuropsychiatric and neurological diseases is justified.

The novelty in this invention is obtaining a tricyclic or tetracyclic molecular system with a diazepine derivative fused DHP ring for potential application in the treatment of cardiovascular, cerebrovascular, neurodegenerative, neuropsychiatric and neurological diseases, as well as the possibility of obtaining these tricyclic or tetracyclic systems using 1,4-dihydropyridine derivatives as a starting material.

BACKGROUND OF THE INVENTION

There are several patents describing benzodiazepine or dihydropyridine derivatives for treating Central Nervous System diseases. In such cases, however, no description is made of the fusion of these nucleuses to form a new pharmacologic entity. Patents using different substituents of the benzodiazepine nucleus, having no relation with the subject matter of our invention are listed below:

Patents EP1593683 and EP1157992 describe the process of obtaining molecules derived from dihydro-2,3-benzodiazepine as potential anticonvulsants, but use hydrogen-type substituents, alkyl chains, and aromatic rings of the phenyl, thienyl, furyl, pyridyl, imidazolinyl, benzimidazolyl, benzothiazole, and pthalazinyl type. Patent EP-349949 describes benzodiazepine-substituted derivatives with heterocyclic groups substituted in turn with aryl, hydroxyl, and carboxyl groups. Patent US20040157833, describes pharmaceutical compounds based on 1-(3,4-dimethoxyphenyl)-4-methyl-5-ethyl-7-methoxy-8-hidroxy-5H-2,3-benzodiazepine.

Patent US20020103371 describes benzodiazepine derivatives modulating the GABA receptor, but does not mention the dihydropyridines.

Patent EP-733634 describes new molecular entities derived from thieno(2,3-B)(1,5) benzodiazepine.

Other patents disclosing benzodiazepine derivatives are the following: U.S. Pat. No. 5,658,901 (yielding 2,3-dihydro-1-(2,2,2-trifluoroethyl)-2-oxo-5-phenyl-1H-1,4 benzodiazepines); U.S. Pat. No. 5,610,158 (yielding 4-oxo- and 4H-imidazo(5,1-c)(1,4)benzoxazines); EP-558104 and GB9201180 (1,5-Benzodiazepine derivatives); EP-491218 (benzodiazepinone derivatives).

Diazepine synthetic variants fused with dihydropyridines, the subject matter of our invention, showed some kind of action upon the Vascular and Central Nervous Systems. However, the degree of the action depends on the nature of the R substituent at the 4-position of the 1,4-DHP and the nature of $R_1$ substituent.

General experimental conditions: NMR-$^1$H and NMR-$^{13}$C spectra, were registered at 25° C. in a Bruker DPX300 spectrometer (300 MHz-$^1$H, 75.4 MHz-$^{13}$C) in DMSO-$d_6$. Mass spectra were obtained with a Hewlett Packard 5989 A purity study was done using a CAMAG TLC-SCNNER II densitometer (Switzerland) ($\lambda$=254 nm).

EXAMPLES OF PROCEDURE

Example 1

Synthesis of the 4-aryl-5-carbonyloxy-6-methyl-2-oxo-1,2,3,4-tetrahydropyridine Synthetic Intermediary Useful for Preparing Compounds of the I, II, III, IV, V, VI, VII, XIII, AND IX Type The 4-aryl-5-carbonyloxy-6-methyl-2-oxo-1,2,3,4-tetrahydropyridines derivatives are part of the synthetic intermediaries required to obtain the final products. In a 100 mL flask provided with a reflux condenser, 5.76 g (40 mmol) of Meldrum acid are dissolved in 40 mL of glacial acetic acid, acetonitrile or ethanol. Then, 40 mmol of the corresponding aromatic aldehyde are added, together with 40 mmol of the given dicarbonyl compound that can be acetyl-acetone, methyl-acetoacetate, ethyl-acetoacetate or any other commercial or previously prepared dicarbonyl compound, and 3.46 g (45 mmol) ammonium acetate. The reaction mixture is heated to reflux for about 8 to 16 hours. Then it is poured into cold water and the precipitated solid is vacuum filtered and recrystallized with ethanol.

Example 2

Synthesis of the Synthetic Intermediary Derived From 4-aryl-5-carbonylacohoxy-6-methyl-2-oxo-1,2,3,4-tetrahydropyridine, Useful for Preparing Compounds of the X, XI, AND XII, Type Method 1
1.44 g (10 mmol) of Meldrum acid are dissolved in 10 mL of glacial acetic acid and 10 mmol of the corresponding aromatic aldehyde are added together with 1.40 g (10 mmol) of another dicarbonyl cyclic compound that could be Dimedone, and 0.7 g (10 mmol) of ammonium acetate. The reaction mixture is heated to reflux for 20 to 35 hours. Once the reaction ends, the mixture is poured into cold water and the precipitated solid is filtered and recrystallized with the proper solvent.
Method 2.
The technique described in EXAMPLE 1, METHOD 1, is used by adding to the mixture of reaction 0.8 mmol, 0.14 g of p-toluensulfonic acid between 4 and 10 hours. The isolation procedure and purification is the same one that for the METHOD 1.

Method 2.
10 mmoles of 5-X-ariliden-derived were dissolved such as 2,2-dimethyl-1,3-dioxane-4,6-dione in 10 mL of glacial acetic acid. To the mixture they are added 1.40 g (10 mmol) of the other necessary dicarbonilic compound (acetilacetone, dimedone, or other) and 0.7 g of ammonium acetate and is refluxed during 2-10 hours. After that, the reaction mixture is added on cold water, and the precipitated solid is filtered and recrystallized with an appropriate solvent.

Example 3

Synthesis of 4-aryl-3-carbonylalcohoxy-2-alkyl-6-chloro-5-formyl-1,4-dihydropyridine Synthetic Intermediary The 4-aryl-3-carbonylalcohoxy-2-alkyl (or aryl)-6-chlorine-5-formyl-1,4-dihydropyridine derivatives are also synthesis intermediaries. To an N,N-dimethylformamide solution in anhydrous chloroform, an equimolar quantity of phosphorus oxychloride is added at room temperature. After a while, a solution of the corresponding 4-aryl-5-carbonylacohoxi-6-alkyl-2-oxo-1,2,3,4-tetrahydropyridine derivative is added. It is then stirred at room temperature for approximately 10-20 hours. Then, a sodium acetate aqueous solution is added and it is stirred for 10 to 30 minutes. The organic phase is separated and the solvent is vacuum-filtered. The solid obtained is recrystallized with ethanol.

Example 4

Synthesis of the Synthetic Intermediary of aryl-3-carboxy-2-methyl-6-chloro-5-formyl-1,4-dihydropyridine (Method A).

In a flask were dissolved in an appropriate organic solvent the derived corresponding of 4-aril-3-carbonilalcohoxi-2-metil-6-chlorine-5-formil-1,4-dihidropiridine, then is added in excess an iorhidrico acid dissolution previously treated with sodium thiosulfate in order to eliminate any impurity. The mixture is refluxed between 8 and 24 hours. After that, the reaction mixture is added in water and the reaction is neutralized with carbonate of sodium or potassium. The precipitated solid is vacuum filtered and washed with small portions of an ethanol/water. Yields 40-75%.

Example 5

Synthesis of the Derived Synthetic Middleman of 4-aryl-3-carboxy-2-methyl-6-chlorine-5-formyl-1,4-dihydropyridine (METHOD B)

The saponification of those derived of 4-aryl-5-carbonylamethoxy-6-methyl-2-oxo-1,2,3,4-tetrahydropyridine is carried out using NaOH, in methanol and water, to those derived of 4-aryl-5-carbanylacarboxy-6-methyl-2-oxo-1,2,3,4-tetrahydropyridine, and following transformation to those derived of 4-aryl-3-carboxy-2-methyl-6-chlorine-5-formyl-1,4-dihydropyridine, by the procedure explained in the Example 3.

Example 6

Synthesis of the Tricyclic and Tetracyclic Systems Derived from Diazepines Fused Dihydropyridines (Compounds Ia II, III, X, XI and XII).

In a flask equipped with magnetic stirring, the corresponding 1,4-dihydropyridiine derivative obtained is dissolved in.

The corresponding 1,2 diamine derivative is then added to the resulting solution. The reaction mixture is stirred at temperatures between 10-78° C. for several hours, till a precipitate appears. This precipitate is filtered and washed with ethanol. For some compounds, isolation of the final products using the column chromatography technique is required.

It is then dried in a desiccator. Yield: 35-80%. Reaction is followed by thin-layer chromatography (ethanol: cyclohexane: chloroform). Compounds are characterized by NMR-H$^1$, NMR-C$^{13}$ and mass spectrometry.

Example 7

Effect of Different Diazepine Fused Dihydropyridines Synthetic Variants on Exploratory Behavior in Mice The open field test has been a widely used test to evaluate drugs with a sedative effect. In this test, the number of rearing and/or crossings of animals in the central area of the open field are quantified. These behaviors are indicative of the exploratory behavior of rodents. Sedative drugs reduce the exploratory behavior of rodents.

The effect of different diazepine fused dihydropyridines synthetic variants on the exploratory behavior was evaluated on Swiss albino rats with 18-22 g of body mass. Animals were administered a 4 mg/Kg dose. After 30 minutes, animals were individually placed in an exploratory activity box for 6 minutes, during which time the number of erections and crossing through the center of the box were recorded.

SUMMARY OF THE INVENTION

The findings of the evaluation of the different molecules tested show a neuro-sedative behavior, though the decrease in the exploratory behavior was not the same in all cases. The difference is due to the structural variations made to the nucleus of the polyheterocyclic system tested. This behavior fits the neuro-pharmachological profile of sedative drugs. The structural nature of the molecules evaluated may justify the resulting effect, due to their potential interaction with the GABAergic receptor.

Figure 1:
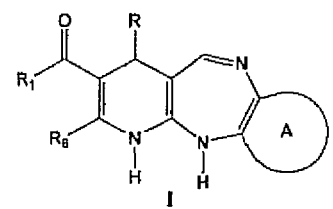
FIG. 1 Global structure of tricyclic and tetracyclic derivates.
Figure 2:
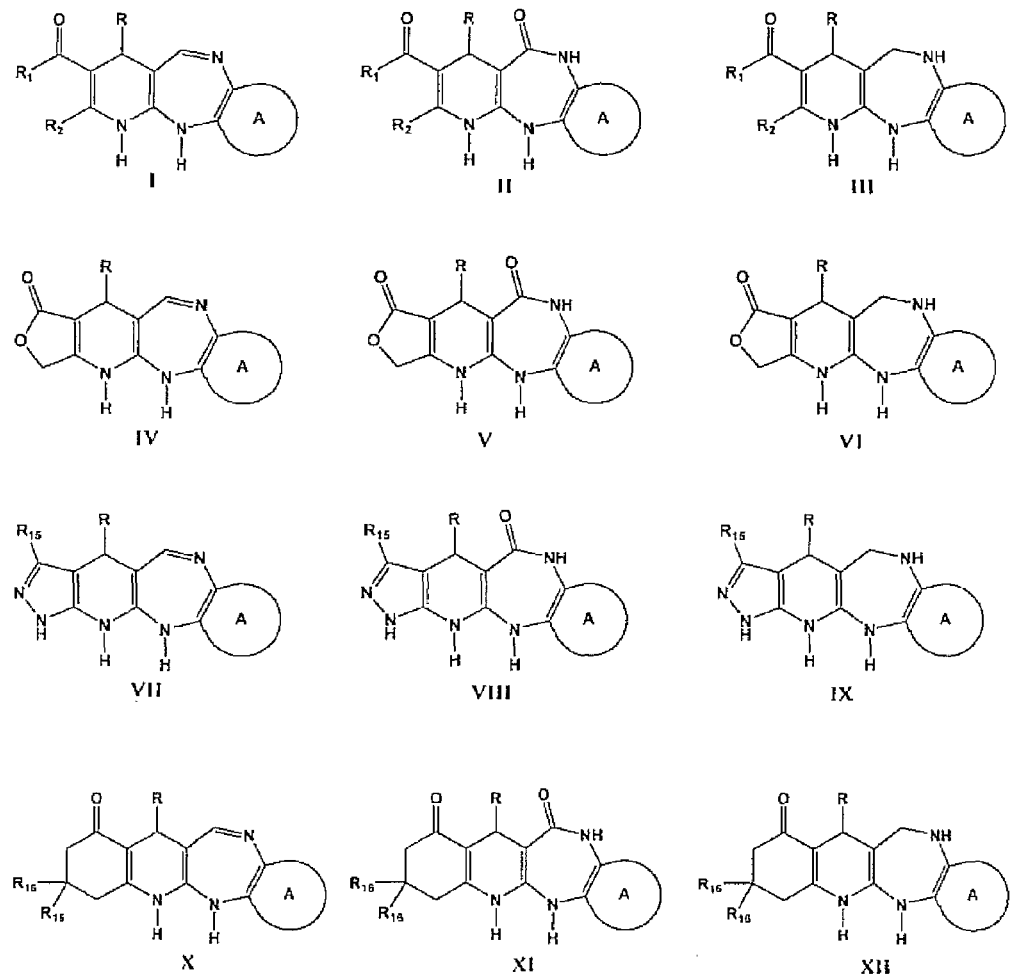
FIG. 2 General formulas of different synthetic variants of diazepine fused dihydropyridines.

The invention claimed is:
1. A tricyclic system comprising at least one of the formula I

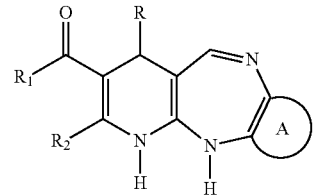

in its racemic modification and as each separately levorotatory and dextrorotatory enantiomer,
wherein for compounds of the formula I; wherein
R comprises a phenyl group, and further comprises
a phenyl substituted with NO$_2$, OH, 3,4-diOH, 2-NO$_2$-3, 4-diOH, F, Cl, 2,3-diCl, 2Cl-5NO$_2$, Br, I, OCH$_3$, CH$_3$, 2-OCOCH$_3$, and OCF$_3$; and further comprises a
-2-pyridyl, -3-pyridyl, or 4-pyridyl;
R$_1$ comprises OR', and wherein R' is an alkyl selected from methyl, ethyl, propyl, isopropyl, butyl, isobutyl, tert-butyl, and 2-cyanoethyl (—(CH$_2$)$_2$—CN);
R$_2$ comprises methyl and;
A comprises a benzene ring alone or with a substituent selected from OH, COOH, CH$_3$, F, Cl, Br and I.

2. A composition comprising one of a tricyclic system comprising at least one of the formula I:

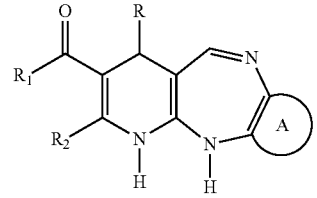

R comprises a phenyl group; and further comprises
a phenyl substituted with NO$_2$, OH, 3,4-diOH, 2-NO$_2$-3, 4-diOH, F, Cl, 2,3-diCl, 2Cl-5NO$_2$, Br, I, OCH$_3$, CH$_3$, 2-OCOCH$_3$, and OCF$_3$ and further comprises a
-2-pyridyl, -3-pyridyl, or 4-pyridyl;
R$_1$ comprises OR', and wherein R' is an alkyl selected from methyl, ethyl, propyl, isopropyl, butyl, isobutyl, tent-butyl, and 2-cyanoethyl (—(CH$_2$)$_2$—CN);
R$_2$ comprises methyl; and
A comprises a benzene ring alone or with a substituent selected from OH, COOH, CH$_3$, F, Cl, Br and I.

3. The composition of claim 2, comprising a racemic mixture of formula I.
4. The composition of claim 2, wherein the composition consists of one of the levo-enantiomer and dextro-enantiomer of the compound of formula I.